US010034609B2

United States Patent
Sun et al.

(10) Patent No.: US 10,034,609 B2
(45) Date of Patent: Jul. 31, 2018

(54) TEMPERATURE SENSOR FOR TRACKING BODY TEMPERATURE BASED ON PRINTABLE NANOMATERIAL THERMISTOR

(71) Applicant: NANO AND ADVANCED MATERIALS INSTITUTE LIMITED, New Territories (HK)

(72) Inventors: Caiming Sun, New Territories (HK); Xiaohua Chen, New Territories (HK)

(73) Assignee: NANO AND ADVANCED MATERIALS INSTITUTE LIMITED, New Territories (HK)

( * ) Notice: Subject to any disclaimer, the term of this patent is extended or adjusted under 35 U.S.C. 154(b) by 325 days.

(21) Appl. No.: 14/932,998

(22) Filed: Nov. 5, 2015

(65) Prior Publication Data

US 2017/0127944 A1    May 11, 2017

(51) Int. Cl.
*A61B 5/00* (2006.01)
*H01C 7/04* (2006.01)
*G01K 1/08* (2006.01)
*G01K 7/22* (2006.01)
*G01K 13/00* (2006.01)
(Continued)

(52) U.S. Cl.
CPC .............. *A61B 5/0008* (2013.01); *A61B 5/01* (2013.01); *G01K 1/08* (2013.01); *G01K 7/22* (2013.01); *G01K 13/002* (2013.01); *H01C 1/142* (2013.01); *H01C 1/1413* (2013.01); *H01C 7/041* (2013.01); *H01C 17/281* (2013.01);
(Continued)

(58) Field of Classification Search
CPC . H01C 7/04; H01C 7/041; G01K 7/22–7/226; G01K 13/002
See application file for complete search history.

(56) References Cited

U.S. PATENT DOCUMENTS 4,276,535 A * 6/1981 Mitsuyu ................. H01C 7/048
                                                 204/192.22
5,090,918 A   2/1992 Zoellick et al.
(Continued)

FOREIGN PATENT DOCUMENTS

CN    2096944 U    2/1992
CN    101413829 A   4/2009
(Continued)

OTHER PUBLICATIONS

Horowitz et al. "The Art of Electronics" published 4/1015.*

*Primary Examiner* — Sean Dougherty
(74) *Attorney, Agent, or Firm* — Wayne & King LLC

(57) ABSTRACT

Provided are wireless temperature sensors. A temperature sensor with a flexible, large-area printed thermistor can include an negative temperature coefficient (NTC) thermistor for temperature sensing, a control circuitry for electrically connecting with the NTC thermistor and obtaining the temperature sensed by the NTC thermistor, a power source for providing power supply to the NTC thermistor and the control circuitry, and a frame element for supporting the NTC thermistor, the control circuitry and the power source, where the frame element is at least partially thermally insulated to establish thermal equilibrium within the temperature sensor. The temperature sensor can sense the temperature in a fast and accurate way due to fast thermal equilibrium established within the sensor.

10 Claims, 12 Drawing Sheets

(51) Int. Cl.
*A61B 5/01* (2006.01)
*H01C 1/142* (2006.01)
*H01C 1/14* (2006.01)
*H01C 17/28* (2006.01)

(52) U.S. Cl.
CPC ............... *A61B 2560/0214* (2013.01); *A61B 2562/0276* (2013.01); *A61B 2562/12* (2013.01); *A61B 2562/164* (2013.01)

(56) References Cited

U.S. PATENT DOCUMENTS

| | | | | |
|---|---|---|---|---|
| 6,257,759 | B1* | 7/2001 | Witonsky | G01K 11/165 |
| | | | | 116/207 |
| 2007/0206655 | A1* | 9/2007 | Haslett | A61B 5/01 |
| | | | | 374/141 |
| 2009/0240022 | A1* | 9/2009 | Uehira | C08G 63/605 |
| | | | | 528/220 |
| 2010/0042013 | A1* | 2/2010 | Cuesta Frau | A61B 5/0008 |
| | | | | 600/549 |
| 2013/0203201 | A1* | 8/2013 | Britton | G01K 7/226 |
| | | | | 438/54 |
| 2014/0121557 | A1* | 5/2014 | Gannon | A61B 5/002 |
| | | | | 600/549 |
| 2015/0007665 | A1* | 1/2015 | Britton | G01K 7/16 |
| | | | | 73/774 |
| 2015/0016487 | A1* | 1/2015 | Britton | G01K 1/20 |
| | | | | 374/185 |
| 2015/0023393 | A1* | 1/2015 | Britton | G01K 7/24 |
| | | | | 374/185 |

FOREIGN PATENT DOCUMENTS

| | | |
|---|---|---|
| CN | 202442810 U | 9/2012 |
| CN | 203773393 U | 8/2014 |
| CN | 104575699 A | 4/2015 |
| CN | 104916379 A | 9/2015 |
| WO | 2010116297 A1 | 10/2010 |

* cited by examiner $V = I_{constant} R_{NTC}$

TEMPERATURE SENSOR FOR TRACKING BODY TEMPERATURE BASED ON PRINTABLE NANOMATERIAL THERMISTOR

TECHNICAL FIELD

This disclosure generally relates to a thermometer field, and particularly to temperature sensors for tracking body temperature based on printable nano-material technology.

BACKGROUND

Smart/wearable devices for body temperature tracking are becoming more and more challenging based on traditional temperature sensing technologies. Electronic sensors for temperature are typically composed of tiny tips of negative temperature coefficient (NTC) ceramic materials, platinum (PT-100) or infrared photo-devices. These electronic sensors don't have enough accuracy for temperature sensing when becoming wearable on a human body since the thermal contact area is limited. It is challenging for these sensors to build up thermal equilibriums with the human body under ambient environments, and thus these thermometers take a very long time to measure the body temperature, such as 10-15 min or much longer. There are also some flexible thin films of platinum sensors for temperature but their area is limited to 1 mm-2 mm since Pt is quite expensive. Therefore, it is very difficult for traditional sensors to continuously monitor and track physiological signals as smart/wearable devices, especially when biometric information on the human body almost changes every second.

SUMMARY OF THIS DISCLOSURE

In one aspect, a temperature sensor based on a printable thermistor can include an negative temperature coefficient (NTC) thermistor for temperature sensing, a control circuitry for electrically connecting with the NTC thermistor and obtaining the temperature sensed by the NTC thermistor, a power source for providing power supply to the NTC thermistor and the control circuitry, and a frame element for supporting the NTC thermistor, the control circuitry and the power source, where the frame element is at least partially thermally insulated to establish thermal equilibrium within the temperature sensor.

The NTC thermistor may include a substrate, a Si—C film printed on the substrate, and electrodes printed on the substrate for electrically connecting the Si—C film with the control circuitry. The NTC thermistor may also include a first laminate arranged on the Si—C film and the electrodes, and a second laminate arranged on a top surface of the first laminate for preventing moisture from penetrating into the NTC thermistor.

In some embodiments, the control circuitry may include a constant current driving circuit which connects with the electrodes of the NTC thermistor. The constant current driving circuit can drive the NTC thermistor with a constant current at a low bias. In this case, the current passing through the NTC thermistor can be kept constant, and thus its operation temperature can be substantially controlled within an allowable range, thereby greatly avoiding a degradation of crosslinking of polymer binders between Si and C nanoparticles within the Si—C film and ensuring a film quality of the printed Si—C film.

In another aspect, a wireless temperature sensor can include an NTC thermistor for temperature sensing, a control circuitry for electrically connecting with the NTC thermistor and obtaining the temperature sensed by the NTC thermistor, a wireless module for receiving the temperature from the control circuitry and sending out the temperature in a wireless way, a power source for providing power supply to the NTC thermistor, the wireless module and the control circuitry, and a frame element for supporting the NTC thermistor, the control circuitry, the wireless module and the power source, where the frame element is at least partially thermally insulated to establish thermal equilibrium within the temperature sensor.

The NTC thermistor may include a substrate, a sensing element, an internal laminate and an external laminate arranged successively. The sensing element can include a Si—C film and electrodes printed on the substrate, where the electrodes connect the Si—C film with the control circuitry. The internal laminate may have a WVTR of substantially 1-100 gam/m$^2$/day and the external laminate may have a WVTR of below substantially 0.1 gram/m$^2$/day, such that the NTC thermistor is prevented from moisture penetration.

The control circuitry can include a constant current driving circuit for driving the NTC thermistor with a constant current, and a measurement circuit for sampling a sensed voltage outputted through the electrodes of the NTC thermistor. The sensed voltage is determined based on the constant current and a resistance of the NTC thermistor.

Various embodiments of this disclosure can provide temperature sensors based on a printable thermistor. The temperature sensors can be configured with excellent thermal insulation, thereby enabling fast and accurate tracking of a body temperature when the temperature sensor is attached to a human body.

BRIEF DESCRIPTION OF THE DRAWINGS

Following detailed descriptions of respective embodiments in this disclosure can be understood better when combining with these figures, in which the same structure is represented by the same reference sign. In the figures.

DETAILED DESCRIPTION

Below this disclosure will be fully described in detail with reference to various embodiments and accompanying drawings.

Temperature sensors (which may also be named as thermometer) for body temperature tracking are provided in various embodiments of this disclosure. Temperature sensing element including silicon-carbon nanocomposite materials may be fabricated into a printed thermistor by printed nanoparticle technology, in order to accurately and fast measure human body temperature. Hybrid laminates with low WVTR and high WVTR can be used to encapsulate the printed thermistor, so as to obtain both optimum curing conditions for printed films and a better lamination for moisture barrier. The temperature sensors can have conformal contact to human skin surface for large-area temperature sensing. Thermal insulation can be formed for the temperature sensor on a backside facing away from the human skin surface, such that fast thermal equilibrium is able to be built up within the thermometer and the sensing for body temperature can be as fast as substantially 1-2 seconds. The thermometer can also be provided with a constant current (CC) driving circuit to control an operation temperature of the printed thermistor.

Figure 1A:
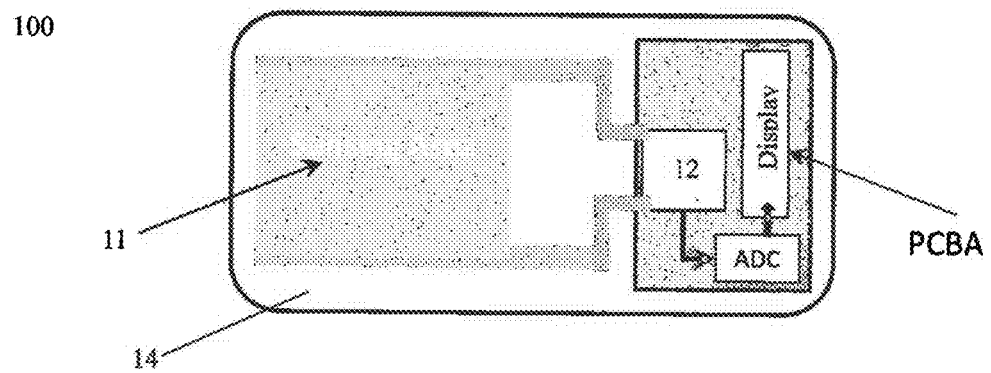
FIG. 1A is a top view of a temperature sensor according to a first embodiment of this disclosure, where the temperature sensor is integrated with a battery and a printed-circuit-board-assembly (PCBA)

FIG. 1A illustrates a temperature sensor 100 according to a first embodiment of this disclosure, where the temperature sensor 100 can include an NTC thermistor 11, a power source, a control circuitry 12 presented as a PCBA and a frame element 14 for supporting the NTC thermistor 11, the power source and the PCBA. The NTC thermistor 11 may operate for sensing a body temperature of a user who wears the temperature sensor 100. It is already known that the thermistor can have different resistances under different temperature, and so the sensed temperature can be determined through a detection of the varying resistance or a varying voltage across the NTC thermistor. The temperature sensed by the NTC thermistor 11 can be read out by the control circuitry 12, and then presented to the user of the temperature sensor 100. The power source can power up the whole temperature sensor 100; that is, it can provide a power supply to the NTC thermistor 11, the control circuitry 12 and any other electronic components within the temperature sensor 100. In some embodiments, a thin lithium battery can be used as the power source without greatly increasing the thickness of the temperature sensor 100. The temperature sensor 100 in this embodiment can further be equipped with a display panel for displaying the sensed temperature to the user.

Figure 1B:
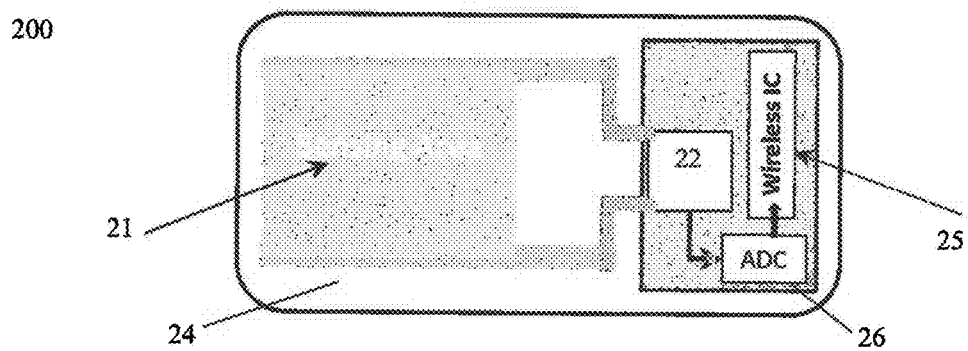
FIG. 1B is a top view of a temperature sensor according to a second embodiment of this disclosure, where the temperature sensor is integrated with a wireless module (wireless IC), a battery and a printed-circuit-board-assembly (PCBA)

FIG. 1B is another embodiment for a temperature sensor 200 of this disclosure. The temperature sensor 200 here can also include an NTC thermistor 21, a power source 23, a control circuitry 22 and a frame element 24, and its operation process for sensing the temperature can be substantially the same as that of the temperature sensor 100. Moreover, the temperature sensor 200 in the second embodiment can further include a wireless module 25 for receiving and then sending out the sensed temperature obtained from the control circuitry 22. The wireless module 25 may be integrated within the PCBA together with the control circuitry 22. In this way, the temperature sensor 200 may cooperate with any other electronic equipment having a wireless receiving unit, so as to reduce its fabrication cost and present the sensed result in a more flexible mode. Below the temperature sensor 200 having the wireless function will be described in detail herein, while its common components with respect to the first embodiment can also be applied to the first embodiment.

Figure 1C:
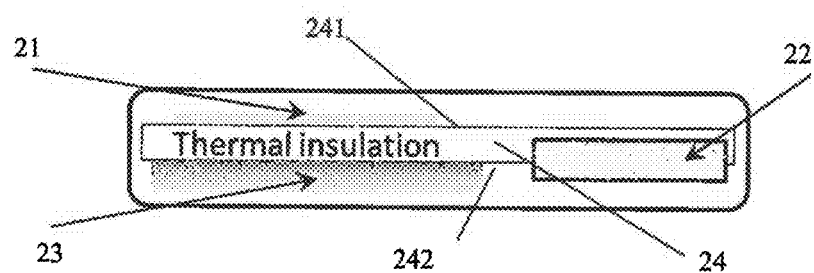
FIG. 1C is a cross-section view of the temperature sensor in FIG. 1B.

As shown in FIG. 1C, it is a cross-section view for the temperature sensor 200. The NTC thermistor 21, the power source 23 and the PCBA (including the control circuitry 22 and the wireless module 25) can be supported on the frame element 24. Specifically, these components can be supported on opposite sides of the frame element 24. The frame element 24 can have a front side 241 facing a body surface of the user and a back side 242 facing away from the body surface, where the front side 241 and the back side 242 are configured oppositely to each other. The NTC thermistor 21 may be arranged on the front side 241 of the frame element 24 to sense the body temperature, while the PCBA and the power source 23 may be arranged on the back side 242 of the frame element 24. The NTC thermistor 21 can be affixed onto the frame element 24. For example, an EVA (or, PVB, PMMA, Silicone) film may function as an adhesive to bond the NTC thermistor 21 onto a surface of the frame element 24. The NTC thermistor 21 can also be mounted on the frame element 24 through any other modes, which will not limit the scope of this disclosure.

Here, the frame element 24 can be at least partially thermally insulated to establish thermal equilibrium within the temperature sensor 200. The frame element 24 can be thermally insulated itself, and/or a thermal insulation structure can be attached onto or embedded within the frame element 24 to establish the thermal equilibrium. The thermal insulation can be enabled for the whole frame element 24; alternatively, one side or one portion of the frame element 24 can be designed to have thermal insulation. In an example, at least the front side 241 and/or the back side 242 of a portion of the frame element 24, for example a portion for arranging the NTC thermistor 21, can be thermally insulated. Due to the thermal insulation configuration, fast thermal equilibrium is able to be built up between the whole thermometer 200 and the human body, and the sensing for body temperature can be as fast as substantially 1-2 seconds. The materials used for thermal insulation may include polyethylene terephthalate (PET), polypropylene (PP), polyethylene (PE), polyvinyl chloride (PVC), polytetrafluoroethylene (PTFE), or other plastics, or some soft rubber sheets with thickness of substantially 0.5 mm-1 mm.

Further referring to FIG. 1B, the NTC thermistor 21 can be a printable thermistor with its sensing area being printed into the temperature sensor 200. The PCBA can bond together with the NTC thermistor 21 through an anisotropic conductive film (ACF) tape. The sensed result can be sampled and amplified by the control circuitry 22, and the processed result will be transferred to the wireless module 25 for transmitting. The control circuitry 22 and the wireless module 25 may be integrated on the PCBA, and they can also electrically connect with the NTC thermistor 21 through the ACF tape. Here, the NTC thermistor 21 can be better prevented from moisture, and the NTC thermistor 21 can be driven using a constant current based on a constant current design of the control circuitry 22.

Figure 2A:
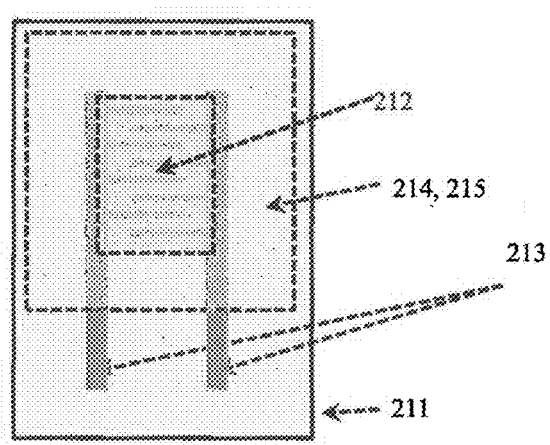
FIG. 2A is a perspective diagram from a top view for a printed thermistor with an encapsulation.
Figure 2B:
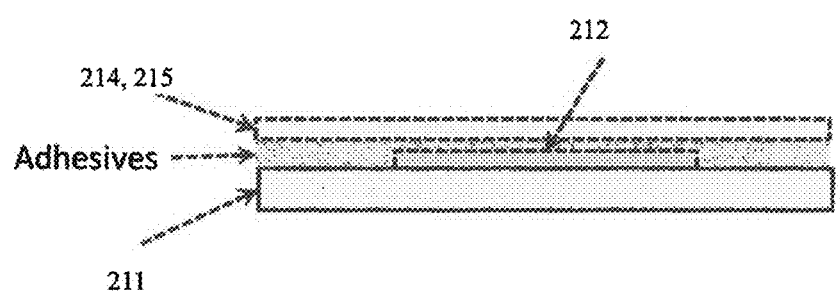
FIG. 2B is a cross-section view of the printed thermistor in FIG. 2B.

FIG. 2A and FIG. 2B respectively illustrate the NTC thermistor 21 which can be used in the temperature sensors 100 and 200 of this disclosure. The NTC thermistor 21 can include a substrate 211, a Si—C film 212 and electrodes 213. In order to improve the moisture prevention, the NTC thermistor 21 can further include a hybrid laminate for encapsulating the Si—C film 212 and the electrodes 213. The Si—C film 212 and the electrodes 213 can function as a sensing element, where both two can be printed onto the substrate 211 and the electrodes 213 can electrically connect the Si—C film 212 with the control circuitry 22. In this disclosure, silicon and carbon nanocomposite materials can be used to produce the printed Si—C film 212, of which a formula and a fabrication process will be described in specific example.

Figure 3:
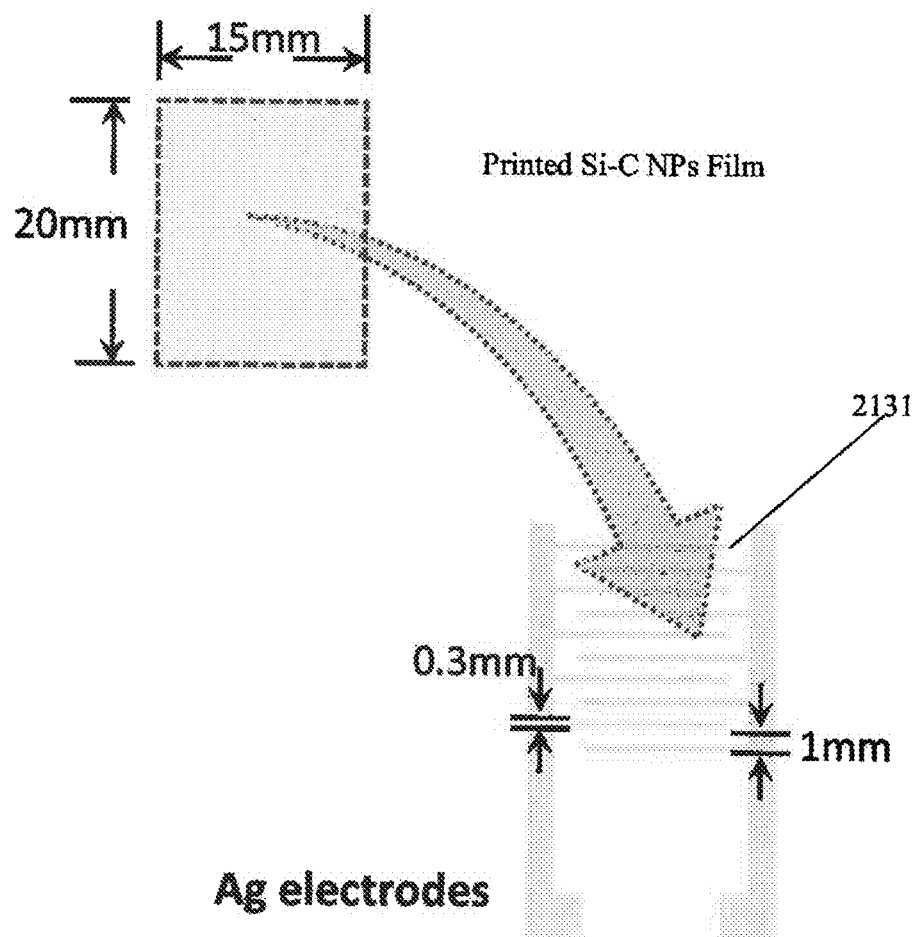
FIG. 3 illustrates a design for a printing process in fabricating a printed thermistor.

FIG. 3 illustrates a design for a printing process in fabricating a printed thermistor. Two interdigitated silver electrodes 213 can be deposited on the LCP substrate 211 using a silver conductor. Ten pairs of fingers 2131 can be prepared for the Ag electrodes 213, with a finger width of about 0.3 mm and an adjacent distance of about 1 mm. The Si—C film with an area of about 15 mm*25 mm may then be defined for Si—C nanocomposite paste printing, and the printed Si—C film may overlap on the fingers 2131 of the electrodes 213. Under this design, the temperature sensors 100 and 200 are able to conformally form thermal contact to the human skin, where the printed sensing element here can form a sensing area of about several $mm^2$ to $m^2$. In a specific example, the sensing area can be about 1.5 cm*2.0 cm to form a large-are temperature sensor in this disclosure.

Silicon and carbon nanoparticles (NPs) are relatively stable under ambient environments, but the temperature sensors based on Si—C NPs need to be encapsulated good enough to prevent moistures from permeating into core devices. Moreover, when flexible temperature sensors work as wearable thermometers, skin moisture is also needed to be prevented from permeating through a surface barrier film in a skin contact area. For this reason, the materials with excellent moisture prevention can be used to fabricate the substrate 211. Also, since the temperature sensor 200 is worn on the body surface, the biocompatibility should be considered as well. In an example, the substrate 211 can be preferably made of liquid-crystal-polymer (LCP), or an LCP film can be preferably used as the substrate 211, due to high interfacial adhesion, biocompatibility, and extremely low degree of moisture absorption of the LCP. Its biocompatibility makes LCP encapsulated sensor be stable on a skin surface and insensitive to human skin, and its moisture barrier property can be defined as a water vapor transmission rate (WVTR) of substantially 0.01 gram/$m^2$/day. In some examples, another laminate, such as an Al foil, can be laminated on an outer surface of the LCP film to further improve the moisture prevention function of the NTC thermistor 21.

The hybrid laminate arranged on the Si—C film 212 and the electrodes 213 can encapsulate the NTC thermistor 21 from a top orientation, and can simultaneously have high and low WVTRs. That is, the Si—C film 212 and the electrodes 213 can be arranged between the substrate 211 and the hybrid laminate. The hybrid laminate can include an internal laminate 214 and an external laminate 215, where the internal laminate 214 is intermediate between the sensing element and the external laminate; i.e., the external laminate 215 and the sensing element are arranged on two opposite sides of the internal laminate 214. In the orientation shown in FIG. 2B, the internal laminate 214 can be directly arranged above the Si—C film 212 and the electrodes 213 and the external laminate 215 arranged on a top surface of the internal laminate 214. The internal laminate 214 can have a high WVTR of substantially 1-100 gram/$m^2$/day. This may provide an optimal thermal curing condition for the NTC thermistor 21, such that better crosslinking of polymer binders can be generated between silicon and carbon NPs, and solvent residues can be further evaporated. The internal laminate 214 can be made of one selected from a group of polyethylene terephthalate, polyimide, polyethylene and so on. The external laminate 215 can have a low WVTR of below substantially 0.1 gam/$m^2$/day, so as to provide excellent moisture prevention function for the NTC thermistor 21. The external laminate 215 can be metal foils (Al, Cu, stainless steel), metallized polymer films, or polymer films with moisture barrier of inorganic oxide coatings (SiOx, AlOx, TiOx, etc. . . . ), and so on.

Figure 4:
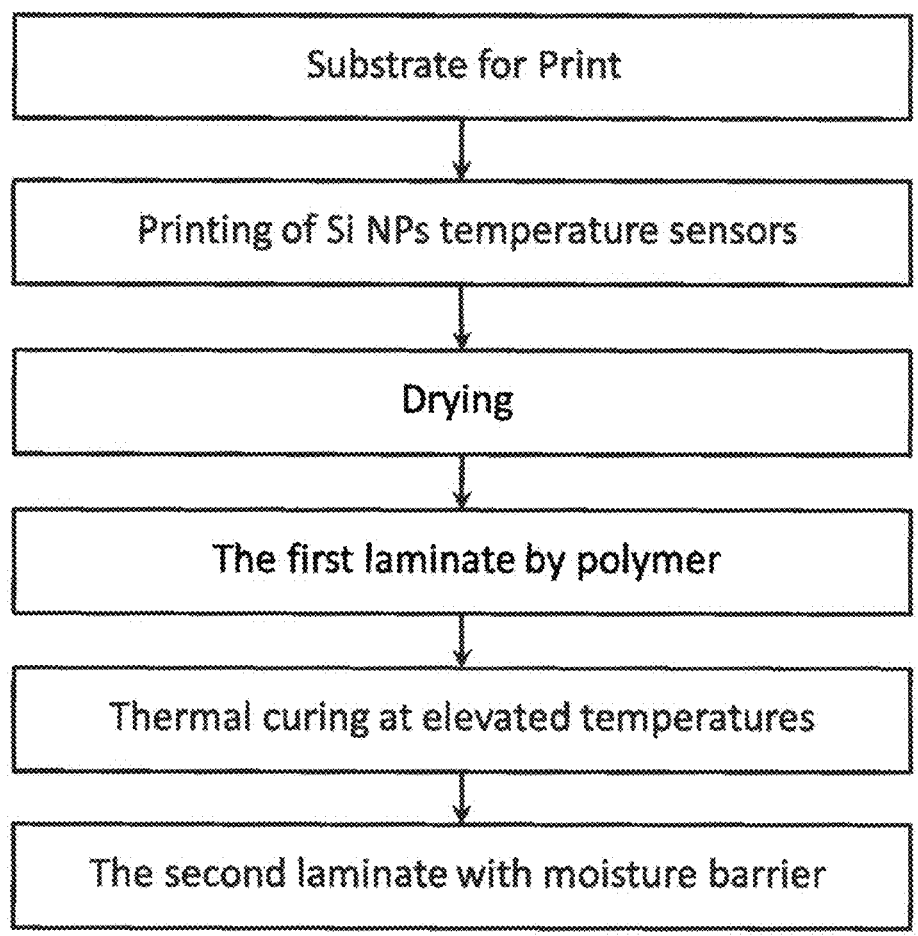
FIG. 4 is a flow chart for fabricating a printed temperature sensor laminated by a moisture barrier according to an embodiment of this disclosure.

In an example (FIG. 4), the electrodes and the Si—C film can be printed onto the substrate successively. After that, a polymer film with a thickness of about 25 μm and with a relatively high WVTR can be laminated on the printed Si—C film 212 and the electrodes 213. Afterwards, thermal curing may be conducted at temperatures of 80° C.-135° C. for 30 min-3 hours in a thermal oven to obtain a first laminate. A second laminate with moisture barrier can then be laminated on the surface of first laminate, name as the second laminate. The second laminate can have quite low WVTR to prevent the NTC thermistor 21 from moisture penetration.

In another example, some other laminate, such as an Al foil, can also be laminated on an outer surface of the external laminate to further improve the moisture prevention function of the NTC thermistor 21.

Referring to FIG. 2A once again, the NTC thermistor 21 with good moisture prevention can electrically connect with the PCBA through its electrodes 213. Correspondingly, the control circuitry 22 can electrically connect with the NTC thermistor 21 through the electrodes 213, so as to sample the sensed temperature.

It is already known that the printed Si—C NPs temperature sensors 100 and 200 may work as negative temperature coefficient (NTC) thermistors. When the NTC thermistors are used for temperature measurement, they may connect to a corresponding measurement circuit. Most frequently, the measurement circuits are voltage dividers or bridge circuits (such as a Wheastone Bridge). However, due to strong nonlinearity of the thermistor characteristic, which is of an exponential type, when the temperature sensor is driven by a Wheastone Bridge, constant voltage (CV) can be applied across the printed Si—C NPs film and with applied voltage fixed, currents passing through the Si—C NPs may increase over one order of magnitude from room temperature to around body temperature. High currents at high temperature will potentially induce additional heating and charging effects within thermistors, and degrade the crosslinking of polymer binders between Si—C NPs and the film quality of the printed Si—C NPs. Therefore, there is the requirement to control the current in a readout system for resistance temperature detectors, in order to extend its operation temperature range.

Figure 5:
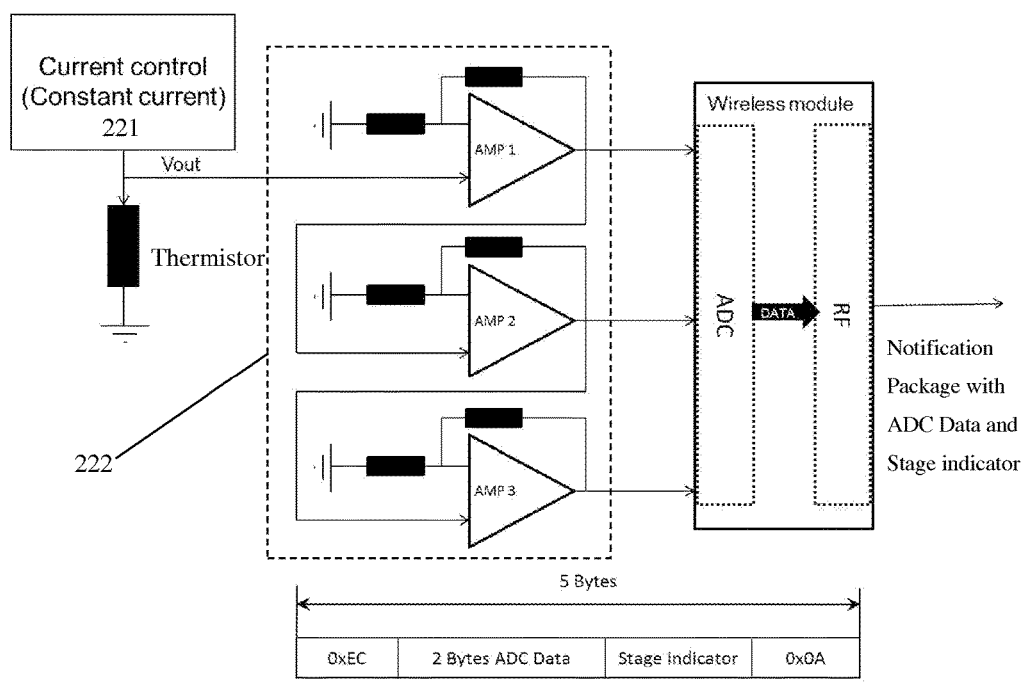
FIG. 5 is a schematic diagram for a control circuitry of a temperature sensor, where the control circuitry functions as both a driving circuit and a readout circuit of a printable thermistor of the temperature sensor.
Figure 6:
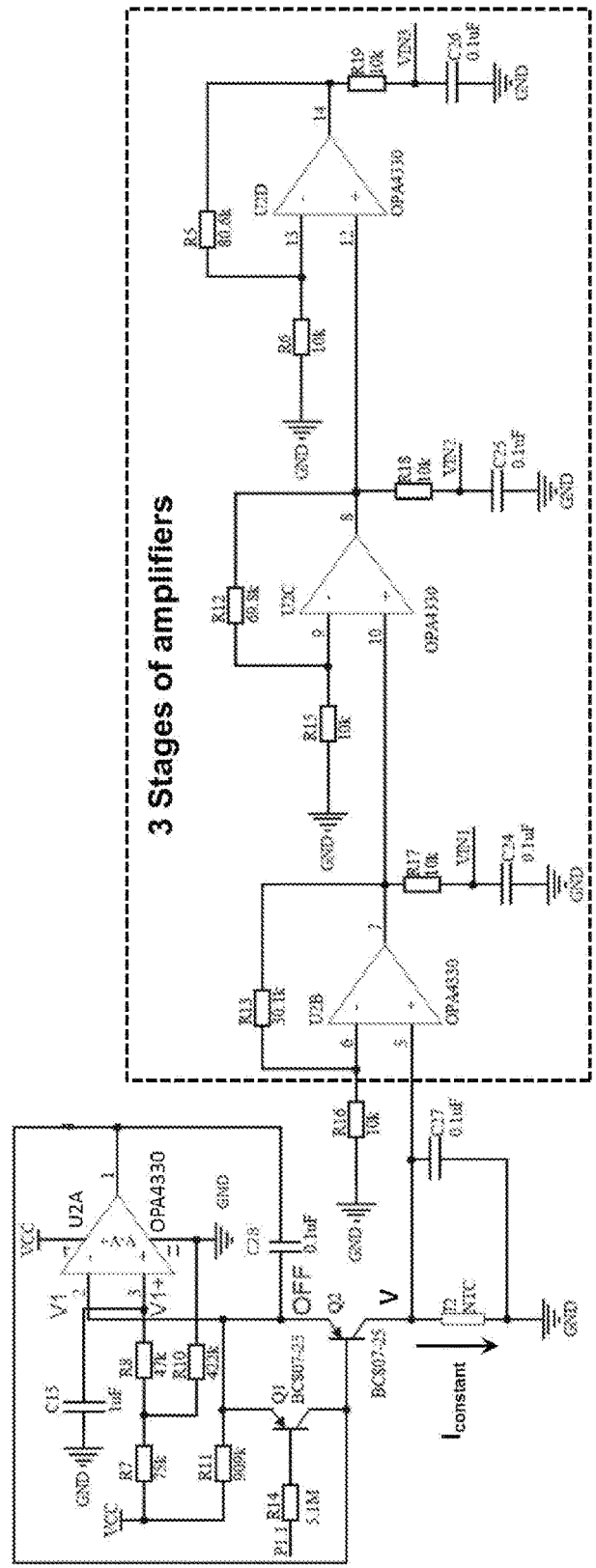
FIG. 6 is a circuit diagram for a control circuitry of a temperature sensor.

For the purpose of current control, a constant current driving circuit 221 can be provided in the control circuitry 22, so as to drive the NTC thermistor 21 with a constant current. A schematic design for a CC bias mode can be found in FIG. 5, while a specific CC driving circuit 221 is schematically shown in FIG. 6. The CC driving circuit 221 can provide the constant current to drive the printed NTC thermistor 21 at a very low bias, so that an operation temperature of the NTC thermistor 21 can be controlled within an allowable range since the current passing through the NTC thermistor 21 can be kept constant.

Under the action of the constant current, the sensed result that is read out from the NTC thermistor 21 can be highly dependent upon its own resistance, which is further determined according to the temperature of the user's body surface. Specifically, the NTC thermistor 21 may generate a sensed voltage varying with the sensed temperature as follows:

$$V=I_{constant}*R_{real-time}$$

where V represents the sensed voltage, the $I_{constant}$ represents the constant current supplied by the CC driving circuit 221, and the $R_{real-time}$ represents a resistance of the NTC thermistor 21 depending on the temperature.

As shown in FIG. 6, an operational amplifier (Op-Amp, Texas Instruments OPA4330) can be used to provide a constant current source to drive the printed Si—C NPs thermistor. A voltage source can be included in the CC driving circuit, where a first driving voltage V1 and a second driving voltage V1+ can be generated by the voltage source. The first driving voltage V1 and the second driving voltage V1+ may be applied to two input ends of the operation amplifier (U2A OPA4330) to provide the bias status for a second transistor Q2 (BC 807-25) at an output end of the operation amplifier. A first transistor Q1 and the second transistor Q2 can form typical internal feedback and generate constant current source to drive the NTC thermistor. In some other example, two respective voltage source can be used to provide the first driving voltage and the second driving voltage to the operation amplifier.

The control circuitry 22 may also include a measurement circuit 222 acting as a readout circuit for the NTC thermistor 21. Here, the measurement circuit 222 can include at least one amplifier for sampling and amplifying the sensed temperature (the sensed voltage in this disclosure) output through the electrodes of the NTC thermistor 21. In an example, three stages of amplifiers (e.g., U2B OPA4330, U2C OPA4330, and U2D OPA4330) are provided in the measurement circuit 222, and a readout $V_{out}$ can be amplified by those three stages of amplifiers for the convenience of transmitting or presentation.

The wireless module 25 can communicate with the control circuitry 22 to obtain the amplified voltage. A Bluetooth module (Texas Instruments CC2541) can be used as the wireless module 25 here. The readout $V_{out}$ can be transferred into the wireless module 25 after amplification. A data converter 26 such as an analog to digital (A/D) converter can be further provided to communicate the control circuitry 22 with the wireless module 25 in this disclosure. After 12-bit A/D conversion, the wireless module 25 can process the converted data to generate a digital package and send out the digital package by an antenna to any other wireless reader. It is noted that although the data converter 26 is exhibited as an embedded component of the wireless module 25, the data converter 26 can also be arranged separated from the wireless module 25. Specific layout of the wireless module 25 and the data converter 26 will not limit the scope of this disclosure.

In another example, a data converter such as an analog to digital (A/D) converter can be provided to communicate the control circuitry 22 with a display component in this disclosure. After 12-bit A/D conversion, the display component can display the converted data for the user.

The above-described embodiments can provide flexible, low-cost and large-area temperature sensors which can realize fast temperature sensing due to excellent thermal insulation. Also, those temperature sensors can further be prevented from moisture penetration effectively and be kept within an allowable operation temperature under the action of the constant current driving.

For more understanding of various embodiments of the temperatures sensors in this disclosure, several examples are provided below to explain such as fabrication process, fabrication formula, material selection, sensor assembly and so on for some specific temperature sensors. Example 1 refers to a fully printable NTC thermistor produced on an 80 μm-thick PET substrate according to the design in FIG. 3. Examples 2 and 3 respectively refer to a fully printable NTC thermistor produced on an LCP substrate according to the design in FIG. 3. Example 4 refers to material selection for the laminate of the NTC thermistor 21. Examples 5 and 6 respectively refer to a full assembly of the temperature sensor with a readout circuitry and a flexible lithium battery according to FIG. 1A and FIG. 1B.

Example 1

Figure 7A:
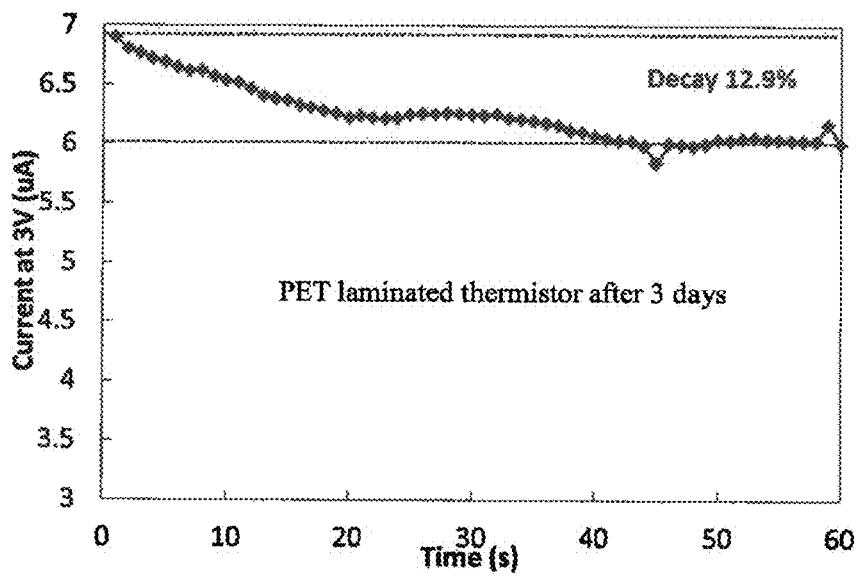
FIG. 7A illustrates DC bias tests for PET-laminated sensors after 80° C./90% RH for 3 days.
Figure 7B:
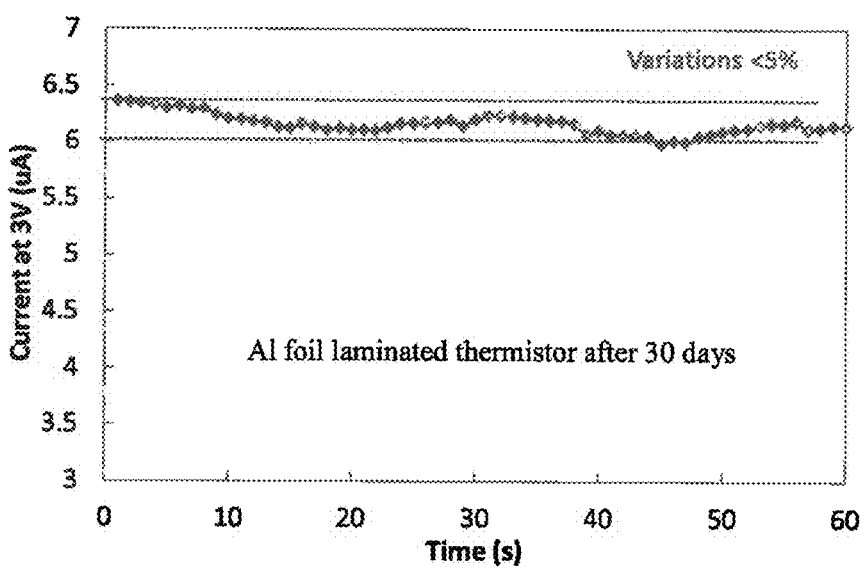
FIG. 7B illustrates DC bias tests for Al foil-laminated sensors after 80° C./90% RH for 30 days.

A fully printable NTC thermistor was produced on an 80 μm-thick PET substrate according to the design in FIG. 3. Two electrodes with a distance of about 1 mm were printed using DuPont 5064H silver conductor material and subsequently cured under ambient conditions. Afterwards, printing paste containing Si NPs and graphite flakes was printed with an area of 15 mm*20 mm, and a continuous film was made to cover above two Ag electrodes (as shown in FIG. 3). The Si—C composites were formed by mixing Si NPs and graphite flakes. The silicon nanoparticles were non-doped silicon nanopowders from MTI Corporation, which had a particle size of about 80 nm and single crystal nanostructures produced by plasma synthesis. The graphite flakes were polar Graphene platelets from Angstron Materials Inc, with thickness of about 10-20 nm and lateral size <14 μm. About 10% graphite flakes were mixed in the Si—C composites. The details of formulas for the Si—C paste were shown as below formula 1. Eventually, the whole mixtures were homogenized in a planetary mixer (Thinky AR-100) for two minutes and a Si—C nanocomposite paste was obtained for screen printing. After printing the Si—C nanocomposite paste, the whole device was dried slowly at room temperature. Then 25 μm-thick polyethylene terephthalate/ethylene-vinyl acetate (PET/EVA) films were laminated on the printed devices by a thermal press bonding process at a temperature of 140° C. and a pressure of 0.9 MPa for 2 min. Afterwards, the whole samples were cured in a thermal oven at 125° C. for 2 hours. After an accelerated tests at 80° C./90% relative humidity (RH) for 3 days, obvious decay under 3V DC bias was observed, around 12.9% within 1 min as FIG. 7A. The moisture may penetrate into the printed Si—C NPs films and degrade the quality of polymer binder. In order to improve the encapsulation for the printed thermistor (PET substrate and PET laminate, named as the first laminate), 25 μm-thick Al foils were laminated on both bottom and top surfaces of above PET-laminated samples by thermal pressing at 140° C. and 0.9 MPa for 2 min (named as the second laminate). The moisture barrier performance of Al foils is much better than that of the PET films and the printed thermistor with Al laminates didn't show obvious decay even after 80° C./90% RH for 30 days. During the DC bias at 3V for 1 min, the variations were smaller than 5% as shown in FIG. 7B.

Formula 1 for forming the Si—C paste:

0.2 gram of diglycidyl ether of bisphenol A (DGEBA) epoxy YD-128 (supplied by Huntsman Corporation) was dissolved into 1 ml acetone by sonication for 10 min;

0.2 gram of polar Graphene powders (supplied by Angstron Materials Inc, N006-P) and 0.3 gram of Si nanopowders were added into epoxy solution by mixing in a planetary mixer (Thinky AR-100) for 2 min;

0.5 gram of Si nanopowders were further added by mixing in a planetary mixer (Thinky AR-100) for 2 min;

the addition of 0.5 g Si NPs was gradually repeated for twice and eventually a total amount of 1.8 g Si NPs were mixed with 0.2 g graphene power homogeneously into epoxy solution;

Acetone was then vaporized from the paste under fume hood for about 30 min;

1 ml analytical grade ethylene glycol (EG) was added as solvent by mixing for 2 min;

60 mg JEFFAMINE D-230 amine was added by mixing for 2 min, where the JEFFAMINE D-230 amine is a polyether diamine acted as a curing agent for epoxy YD-128, supplied by Huntsman Corporation.

EG (0.2 ml by every time) was gradually added until the viscosity is appropriate for screen printing, and the paste was defoamed for 2 min using Thinky AR-100.

Example 2

Figure 8A:
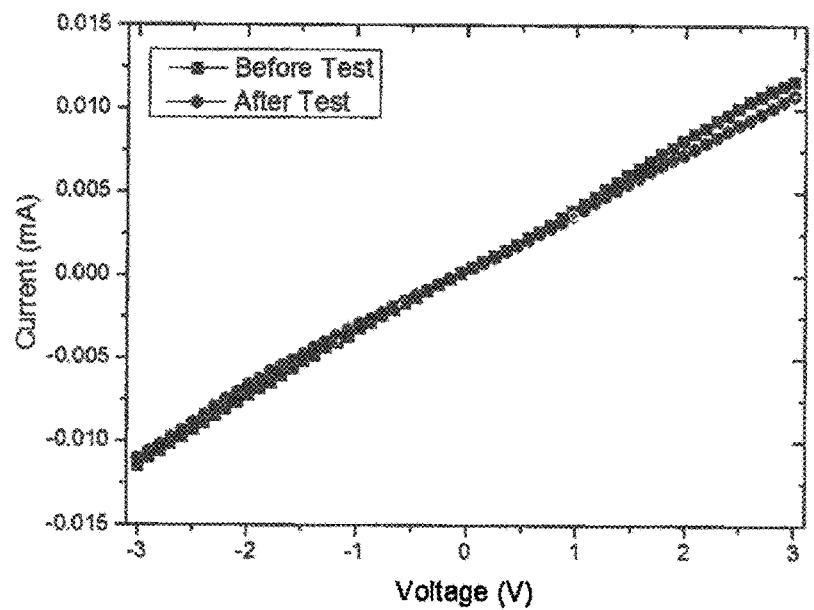
FIG. 8A illustrates current versus voltage (IV) measurements before/after accelerated tests at 80° C./90% RH for 213 hours.
Figure 8B:
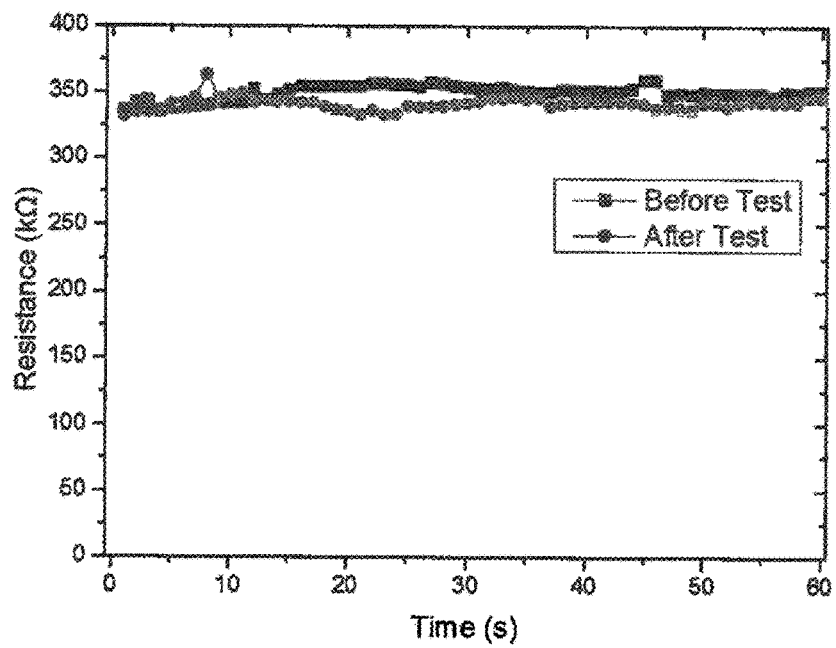
FIG. 8B illustrates resistance measurements before/after accelerated tests at 80° C./90% RH for 213 hours.
Figure 9:
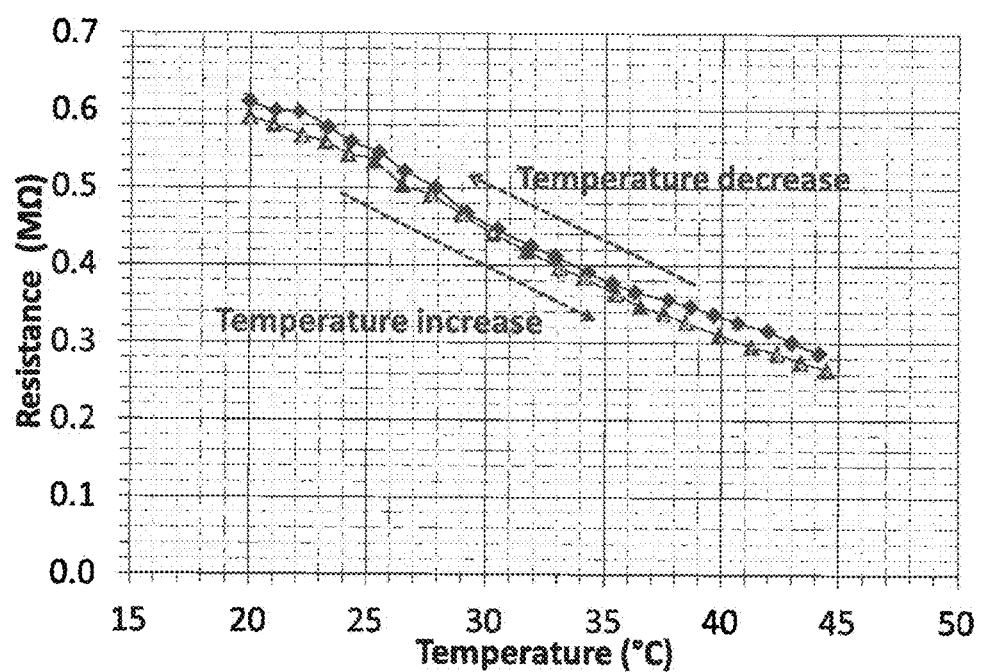
FIG. 9 illustrates resistance versus temperature measurements for an NTC thermistor during temperature increase/decrease loops.

In a second example, another fully printable NTC thermistor was produced according to the design in FIG. 3. Two interdigitated silver electrodes were deposited on a 50 μm-thick LCP substrate by screen printing using DuPont 5064H silver conductor. Ten pairs of fingers were prepared for the Ag electrodes, with finger width of about 0.3 mm and adjacent separation of about 1 mm. Then, an area of 15 mm*25 mm was defined for Si—C nanocomposite paste printing. The Si—C composites were formed by mixing Si NPs and graphite flakes. The silicon nanoparticles were non-doped silicon nanopowders from MTI Corporation, which had a particle size of about 80 nm and single crystal nanostructures produced by plasma synthesis. The graphite flakes were polar Graphene platelets from Angstron Materials Inc, with thickness of about 10-20 nm and lateral size below 14 μm. About 10% graphite flakes were mixed in Si—C composites. The formula for the Si—C paste was followed as formula 1 described above. The 25 μm-thick PET/EVA was used as a first laminate by thermal pressing at 140° C. and 0.9 MPa for 2 min. Then the whole sample was cured in a thermal oven at 125° C. for 2 hours. Dual-layer of PET/Al/EVA was applied as a second laminate on the surface of PET laminate by thermal pressing at 140° C. and 0.9 MPa for 2 min. Accelerated tests at 80° C./90% RH were conducted for these samples with strong lamination. They were able to pass over 213 hours accelerated tests at 80° C./90% RH, From FIG. 8A, current versus voltage (IV) measurement was conducted for these samples before and after 80° C./90% RH for 213 hours. It was found that the deviations of these two IV curves were very small (i.e., <5%). The resistance at 3V DC bias also varied very little after accelerated tests at 80° C./90% RH, as shown in FIG. 8B. Resistance versus temperature (R-T) for these thermistors was measured during temperature increase and decrease loops in 20° C.-45° C. (FIG. 9). In this temperature changing loop, R-T curves shift very little (<0.3° C.) considering the accuracy of testing system is +/−0.5° C.

Example 3

Figure 10A:
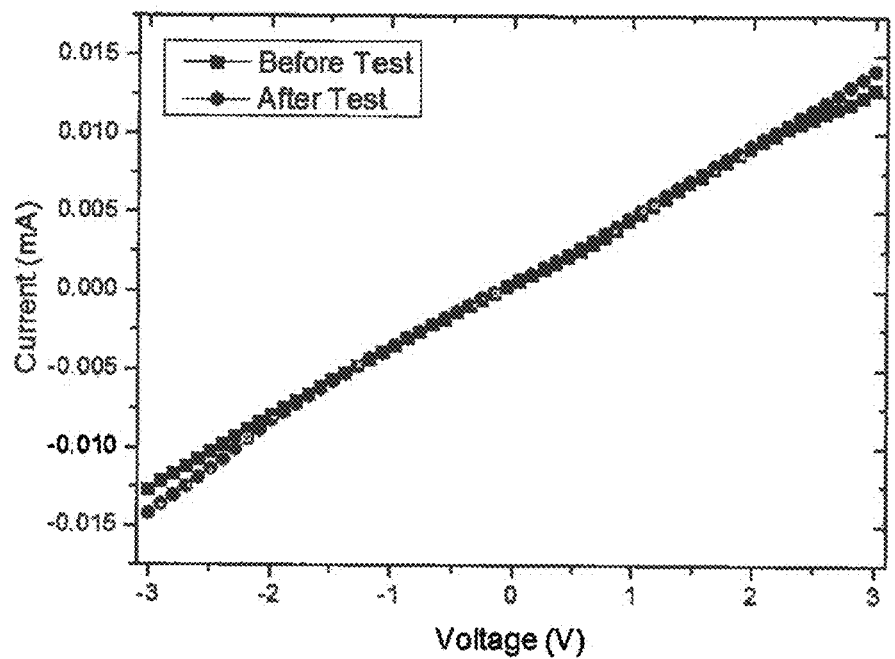
FIG. 10A illustrates current versus voltage (IV) measurements before/after accelerated tests at 80° C./90% RH for 250 hours.
Figure 10B:
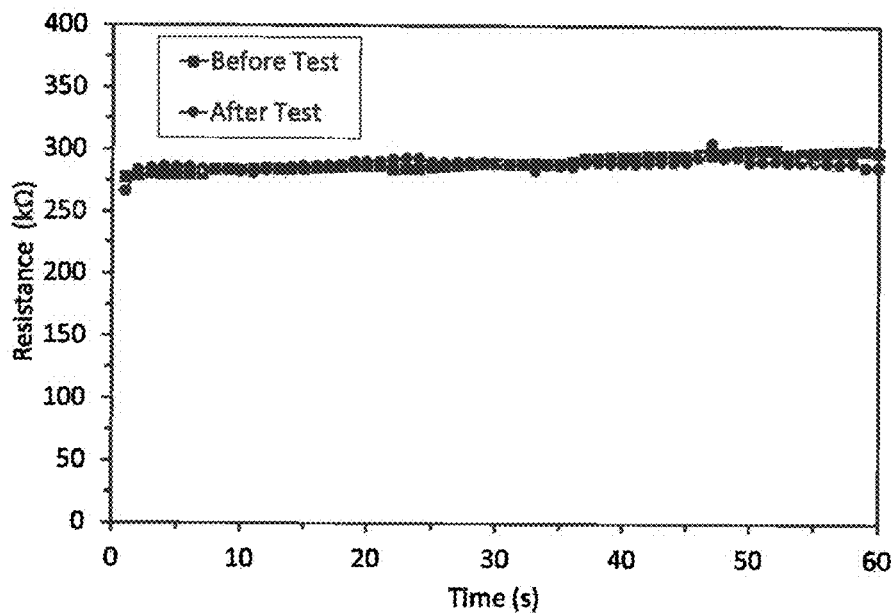
FIG. 10B illustrates resistance measurements before/after accelerated tests at 80° C./90% RH for 250 hours.

In a third example, still another fully printable NTC thermistor was also fabricated according to the design in FIG. 3. Two interdigitated silver electrodes were deposited on a 50 μm-thick LCP substrate by screen printing using DuPont 5064H silver conductor. Ten pairs of fingers were prepared for the Ag electrodes, with finger width of about 0.3 mm and adjacent separation of about 1 mm. Then, an area of 15 mm*25 mm was defined for Si—C nanocomposite paste printing. The Si—C composites were formed by mixing Si NPs and graphite flakes. The silicon nanoparticles were non-doped silicon nanopowders from MTI Corporation, which had a particle size of about 80 nm and single crystal nanostructures produced by plasma synthesis. The graphite flakes were polar Graphene platelets from Angstron Materials Inc, with thickness of about 10-20 nm and lateral size below about 14 μm. About 10% graphite flakes were mixed in Si—C composites. The formula for Si—C paste was followed as formula 1 described above. The 25 μm-thick PET/EVA was used as a first laminate by thermal pressing at 140° C. and 0.9 MPa for 2 min. Then the whole sample was cured in thermal oven at 125° C. for 2 hours. The 50 μm-thick LCP film was applied as a second laminate on the surface of the PET laminate via films of EVA adhesives by thermal pressing at 140° C. and 0.9 MPa for 2 min. Accelerated tests at 80° C./90% RH were conducted for these samples with LCP laminates. They were able to pass over 250 hours accelerated tests at 80° C./90% RH. From FIG. 10A, currents versus voltage (IV) measurement was conducted for these samples before and after 80° C./90% RH for 250 hours. It was found that the deviations of these IV curves were very small (i.e., <5%). The resistance at 3V DC bias also varied very little after accelerated tests at 80° C./90% RH for 250 hours, as shown in FIG. 10B.

Example 4

Figure 11A:
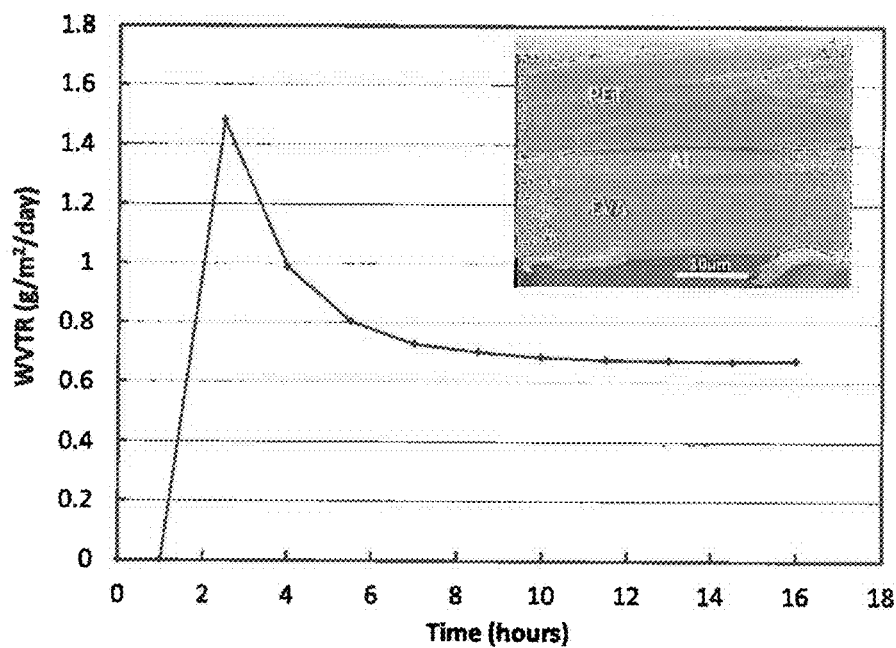
FIG. 11A illustrates WVTR tests of PET/Al/EVA films with a cross-sectional SEM image for the PET/Al/EVA films.
Figure 11B:
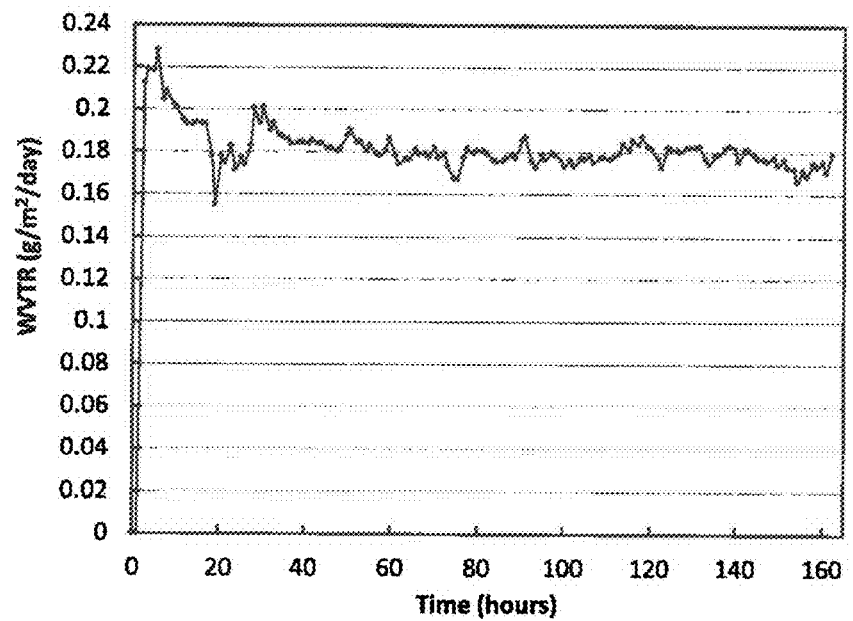
FIG. 11B illustrates WVTR measurements for 50 μm-thick LCP films.

In order to find suitable laminates for printed Si—C NPs sensors, properties of moisture penetration were studied for different films, including PET, PI, PET/EVA, PET/Al/EVA (a thin Al film of 3 μm), liquid crystal polymer (LCP), Al foils, Cu foils, etc. . . . The water vapor transmission rate (WVTR) was measured by MOCON 3/33MA at 38° C. 100% RH. FIG. 11A showed WVTR measurement results for 25 μm-thick PET/Al/EVA films. The PET/Al/EVA films were tested to have a WVTR of 0.673002 g/m$^2$/day at 38° C. 100% RH, and the 3 μm-thick Al was verified as an SEM image of sandwich structures for the PET/Al/EVA film. The WVTR of the 50 μm LCP films was 0.179296 g/m$^2$/day at 38° C. 100% RH as shown in FIG. 11B. The WVTR for more films were measured as shown in Table 1 for reference. Al foils and Cu foils have the WVTR below the detection limit of MOCON 3/33MA, $5*10^{-3}$ g/m$^2$/day. Multiple layers of PET/Al/EVA can be laminated together in order to obtain much lower WVTR. Dual-layer of 25 µm PET/Al/EVA films have the WVTR as low as 0.267845 g/m²/day and five-layer of 25 µm PET/Al/EVA films are able to provide better moisture barrier with WVTR of 0.073883 g/m²/day.

TABLE 1

WVTR results for different films

| Material | WVTR at 38° C. 100% RH (g/m²/day) |
|---|---|
| 25 µm PET/Al/EVA (1-layer 3 µm Al foil) | 0.673002 |
| 25 µm PET/Al/EVA (2-layer 3 µm Al foil) | 0.267845 |
| 25 µm PET/Al/EVA (5-layer 3 µm Al foil) | 0.073883 |
| 15 µm Al film | <0.005 |
| 25 µm Al film | <0.005 |
| 25 µm Cu film | <0.005 |
| 100 µm PET film | 6.48736 |
| 25 µm PET/EVA | 84.81131 |
| 60 µm PET/EVA | 18.91197 |
| 50 µm Polyimide (PI) film | 41.19716 |
| 50 µm Liquid Crystal Polymer (LCP) | 0.179296 |

Example 5

In a fifth example, a full assembly of a temperature sensor with a readout circuitry and a flexible lithium battery was presented according to the design shown in FIG. 1A. 15 mm*20 mm temperature thermistor with a LCP substrate and a PET/Al laminate (similar to the thermistor in the example 2) was bonded on a 0.5 mm-thick PP frame with good thermal insulation. EVA film as thin as 50 µm on the surface of the PP frame functions as an adhesives for bonding the thermistor on the surface by thermal pressing at 130° C. and 0.1 MPa for 1 min. The PP frame is about 35 mm wide and 60 mm long, with the thermistor mounted on one side and a PCBA with the battery connected mounted on the other side of the PP frame. An anisotropic conductive film (ACF) tape (3M 9703) was used to bond Ag electrodes of the printed thermistor to PCB pads at 70° C. and 0.1 MPa. The flexible battery (lithium-ceramic battery, model no. FLCB033034 AH1XAA, supplied by Prologium Technology Co. Ltd.) was used to power up the whole sensor system. They have nominal capacity of about 10.5 mAh, nominal voltage of about 3.7V, and thickness of about 0.35 mm. The lithium battery is rechargeable and connected to power supply pads arranged through solder welding on the PCBA. The PCBA in this example had a dimension of about 15 mm*35 mm. The readout circuitry for sensor data was schematically shown in FIG. 6. The printed thermistor was biased by an operational amplifier (U2A OPA4330). Its output voltage Vout was amplified by three-stage amplifiers U2B OPA4330, U2C OPA4330, and U2D OPA4330. Then the amplified signals were transferred into a Bluetooth module (Texas Instruments CC2541).

Figure 12:
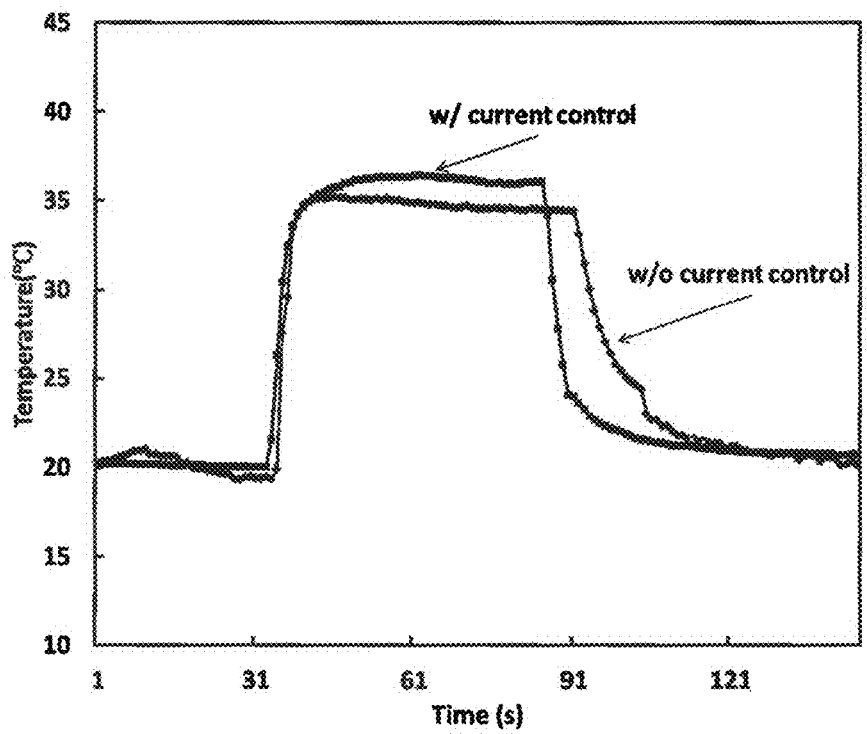
FIG. 12 shows temperature responses of temperature sensors with current control (CC mode) versus without current control (CV mode)

According to the circuit design in FIG. 6, a constant current of as low as 0.5 µA was used to bias the large-area thermistor (which can be named as a CC mode). Current control was critical to long-term reliability and high accuracy of the temperature sensor. In order to explain the effect of the current control, the printed thermistors were biased with current control (CC mode) versus without current control (CV mode) in FIG. 12. When the thermistor was heated up from room temperature to body temperature, the sensor system with current control is fast and accurately tracking temperature changes. But as demonstrated in FIG. 12 the printed thermistor biased at a constant voltage (CV) of 3V cannot follow this temperature increase and decrease. The printable NTC sensors may degrade a little bit at high temperature because they operate without any current control and high currents pass through the large-area printed films.

Example 6

Figure 13:
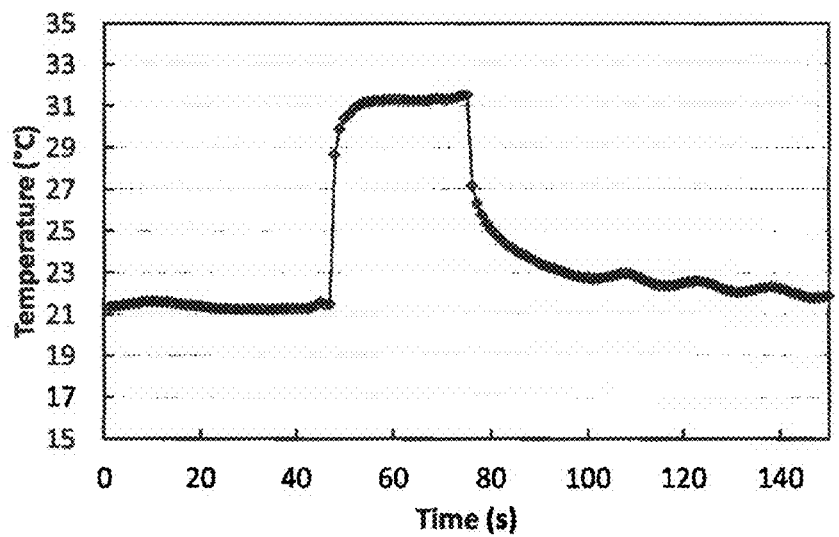
FIG. 13 shows fast responses of wireless thermometer with large-area thermistor and backside thermal insulation.

In a sixth example, another full assembly of a temperature sensor with a readout circuitry and a flexible lithium battery was also presented according to FIG. 6. 15 mm*20 mm temperature thermistor with a LCP substrate/LCP laminate (similar to the thermistor in the example 3) was bonded on a 0.5 mm-thick PP frame with good thermal insulation. An EVA film as thin as 50 µm on a surface of the PP frame functions as an adhesive for bonding the thermistor on the surface by thermal pressing at 130° C. and 0.1 MPa for 1 min. The PP frame is about 35 mm wide and 60 mm long, with the thermistor mounted on one side and a PCBA with the battery connected mounted on the other side of the PP frame. An anisotropic conductive film (ACF) tape (3M 9703) was used to bond Ag electrodes on the printed thermistor to PCB pads at 70° C. and 0.1 MPa. Flexible batteries (lithium polymer battery 062329S, supplied by Guangzhou Fullriver Battery New Technology Co., Ltd) were used to power up the whole sensor system. They have nominal capacity of about 20 mAh, nominal voltage of about 3.7V, and thickness of about 0.7 mm. These lithium batteries are rechargeable and connected to power supply pads on the PCBA. Constant current of about 5 µA was used to bias the large-area thermistor (CC mode). When hand fingers touch the contact area of the wireless thermometer, it responses as fast as 1 s in FIG. 13 and after several seconds it eventually settles down. It is found that both temperature increase and decrease can finish within 1-2 seconds.

In various embodiments and examples of this disclosure, the NTC thermistor with the LCP substrate and the hybrid laminate can be provided, such that the NTC thermistor can be prevented from the moisture from both a top and a bottom surface. In various embodiments and examples of this disclosure, the temperature sensor (especially wireless one) can be provided to have excellent thermal insulation and current control, such that the temperature sensor can sense the temperature in a faster and more accurate operation.

In various embodiments and examples of this disclosure, the NTC thermistors, the laminates, or the frames may be described to have the top surface and the bottom surface. It is noted that the terms of "top" and "bottom" are defined with respect to the human body surface to which the temperature sensor is attached. The surface facing the human body surface can be defined as the top surface, while the one facing away from the human body surface can be defined as the bottom surface; and vice versa.

In various embodiments and examples of this disclosure, the NTC thermistors, the laminates, or the frames may be described to have the front side and the back side. It is noted that the terms of "front side" and "back side" are defined with respect to the human body surface to which the temperature sensor is attached. The side facing the human body surface can be defined as the front side, while the one facing away from the human body surface can be defined as the back side.

Although the frames in the figures are shown to be a planar structure, these figures are only schematic for displaying the arrangement of the NTC thermistor, the battery and the PCBA on the frame. Alternatively, the frame may function as support the necessary components of the temperature sensor, and keep some internal components such as the PCBA and the battery from exposing to the user. Specific designs for the frame will not limit the scope of this disclosure.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Many other changes and modifications may be made to this disclosure without departing from the spirit thereof. The scope of these and other changes will become apparent from the appended claims.

The invention claimed is:

1. A temperature sensor based on printable thermistor, comprising:
   a negative temperature coefficient (NTC) thermistor for temperature sensing, which comprises a substrate, a Si—C film printed on the substrate, and electrodes printed on the substrate for connecting the Si—C film with a control circuitry; wherein the NTC thermistor further comprises a first laminate and a second laminate; the first laminate is directly arranged on the Si—C film and the electrodes and is configured to improve thermal curing for the NTC thermistor; the second laminate is arranged on one side of the first laminate opposite to the Si—C film and the electrodes and is configured to prevent moisture from penetrating into the NTC thermistor;
   the control circuitry which electrically connects with the NTC thermistor and operates for obtaining the temperature sensed by the NTC thermistor;
   a power source for providing power supply to the NTC thermistor and the control circuitry; and
   a frame element for supporting the NTC thermistor, the control circuitry and the power source; wherein the frame element is at least partially thermally insulated to establish thermal equilibrium within the temperature sensor.

2. The temperature sensor of claim 1, wherein the first laminate has a water vapor transmission rate (WVTR) of 1-100 gram/m²/day and the second laminate has a WVTR of below 0.1 gram/m²/day; and/or
   the first laminate is made of one selected from a group of polyethylene terephthalate, polyimide, polyethylene; and the second laminate is one selected from a group of a metal foil, a metallized polymer film, and a polymer film with a inorganic oxide coating.

3. The temperature sensor of claim 1, wherein the control circuitry comprises a constant current driving circuit which drives the NTC thermistor with a constant current, and the NTC thermistor generates a sensed voltage varying with the temperature as follows:

$$V = I_{constant} * R_{real-time};$$

where V represents the sensed voltage, the $I_{constant}$ represents the constant current supplied by the constant current driving circuit, and the $R_{real-time}$ represents a resistance of the NTC thermistor depending on the temperature.

4. The temperature sensor of claim 3, wherein the constant current circuit comprises an operation amplifier at least one voltage sources, a first transistor and a second transistor; a first driving voltage and a second driving voltage generated by the at least one voltage sources are respectively applied to two input ends of the operation amplifier to provide a bias for the second transistor at an output end of the operation amplifier; the first transistor and the second transistor are connected into an internal feedback circuit to generate the constant current for the NTC thermistor.

5. The temperature sensor of claim 3, wherein the control circuitry further comprises a measurement circuit; the measurement circuit comprises at least one amplifier for sampling and amplifying the sensed voltage output through the electrodes of the NTC thermistor.

6. The temperature sensor of claim 5, furthering comprising a wireless module and a data converter communicated with the control circuitry; the amplified voltage is converted by the data converter to generate a data package, and the data package is transferred to the wireless module for transmitting; wherein the wireless module selects from a group comprising a Bluetooth module, a WiFi module, a Zigbee module or a radio frequency identification (RFID) module.

7. The temperature sensor of claim 1, wherein the Si—C film has a conformal contact surface for the temperature sensing, and the conformal contact surface has an area of 1-2 cm²;
   and/or,
   the substrate is a liquid-crystal-polymer (LCP) film with a WVTR of 0.01 gram/m²/day.

8. The temperature sensor of claim 1, wherein the frame element has a front side and a back side which two are configured oppositely to each other; the NTC thermistor is arranged on the front side of the frame element, and the control circuitry and the power source are arranged on the back side of the frame element;
   at least a portion of the frame element for arranging the NTC thermistor is made of polytetrafluoroethylene, polyethylene terephthalate, polypropylene, polyvinyl chloride, polyethylene or rubber; and/or a thermal insulation structure is at least disposed on the front side of the frame element corresponding to a portion of the frame element for arranging the NTC thermistor.

9. A wireless temperature sensor, comprising:
   an NTC thermistor for temperature sensing, which comprises a substrate, a sensing element, an internal laminate and an external laminate arranged successively; the sensing element comprises a Si—C film and electrodes printed on the substrate, wherein the electrodes connect the Si—C film with a control circuitry;
   the internal laminate has a WVTR of 1-100 gram/m²/day such that the NTC thermistor is provided with improved thermal curing, and the external laminate has a WVTR of below 0.1 gram/m²/day, such that the NTC thermistor is prevented from moisture penetration;
   the control circuitry, which electrically connects with the NTC thermistor and operates for obtaining the temperature sensed by the NTC thermistor; the control circuitry comprises a constant current driving circuit for driving the NTC thermistor with a constant current, and a measurement circuit for sampling a sensed voltage output through the electrodes of the NTC thermistor, wherein the sensed voltage is determined based on the constant current and a resistance of the NTC thermistor;
   a wireless module for receiving the sensed voltage from the control circuitry and sending out the sensed voltage in a wireless way;

a power source for providing power supply to the NTC thermistor, the control circuitry and the wireless module; and a frame element for supporting the NTC thermistor, the control circuitry, the power source and the wireless module; wherein the frame element is at least partially thermally insulated to establish thermal equilibrium within the temperature sensor.

10. The temperature sensor of claim 1, wherein the electrodes are deposited on the substrate to form multiple pairs of fingers, and a gap is provided between each adjacent pairs of the fingers; wherein the Si—C film overlap on each gap between the fingers of the electrodes.

* * * * *